United States Patent [19]

Edwards et al.

[11] Patent Number: 5,749,846
[45] Date of Patent: *May 12, 1998

[54] MEDICAL PROBE DEVICE WITH OPTICAL VIEWING CAPABILITY

[75] Inventors: Stuart D. Edwards, Los Altos; Hugh R. Sharkey, Redwood City; Ingemar H. Lundquist, Pebble Beach; Ronald G. Lax, Grass Valley; James Allen Baker, Jr., Palo Alto, all of Calif.

[73] Assignee: Vidamed, Inc., Fremont, Calif.

[*] Notice: The term of this patent shall not extend beyond the expiration date of Pat. No. 5,435,805.

[21] Appl. No.: 485,802

[22] Filed: Jun. 7, 1995

Related U.S. Application Data

[63] Continuation of Ser. No. 62,364, May 13, 1993, Pat. No. 5,435,805, which is a continuation-in-part of Ser. No. 929,638, Aug. 12, 1992, abandoned, and Ser. No. 12,370, Feb. 2, 1993, Pat. No. 5,370,675.

[51] Int. Cl.⁶ ........................................ A61B 17/39
[52] U.S. Cl. ........................................ 604/22
[58] Field of Search ........................ 604/19–22, 53, 604/164, 280; 601/2; 606/39, 45, 32, 47, 48; 607/96, 113, 115, 116, 138, 156, 101, 102

[56] References Cited

U.S. PATENT DOCUMENTS

| | | |
|---|---|---|
| 2,008,526 | 7/1935 | Wappler et al. |
| 2,028,635 | 1/1936 | Wappler |
| 2,038,393 | 4/1936 | Wappler |
| 4,016,886 | 4/1977 | Doss et al. |
| 4,474,174 | 10/1984 | Petruzzi |
| 4,524,770 | 6/1985 | Orandi |
| 5,435,805 | 7/1995 | Edwards et al. ............ 604/22 |

OTHER PUBLICATIONS

Greenwald Surgical Company, Inc., "Orandi Resectoscope Injection Needle for Injection of Local Anesthetics," (Undated) Sheet No. P000121.

E.F. Nation, M.D., "Evolution of Knife–Punch Resectoscope," (Apr. 1976) Urology, vol. VII, No. 4, pp. 417–427.

R. Gutierrez, "Transurethral Treatment of Bladder Neck Obstructions: Endoscopic Prostatic Resection," (Apr. 1933) History of Urology, vol. II, Chapter V, pp. 137–186.

C.W. Ogden, Heat and the Prostate from Electrolysis to Microwaves: Lessons from an Historical Perspective, (Undated) Abstract, 2 sheets, p. 366.

(List continued on next page.)

*Primary Examiner*—Michael Buiz
*Assistant Examiner*—Manuel Mendez
*Attorney, Agent, or Firm*—Flehr Hohbach Test Albritton & Herbert LLP

[57] ABSTRACT

A medical probe device comprising a catheter having a stylet guide housing with at least one stylet port in a side thereof and stylet guide means for directing a flexible stylet outward through at least one stylet port and through intervening tissue to targeted tissues. The stylet guide housing has an optical viewing means positioned for viewing the stylet and adjacent structure which includes a fiber optic channel means for receiving a fiber optic viewing device. The fiber optic channel means can include a guide port means for directing longitudinal movement of a fiber optic device with respect to the stylet guide means in a viewing zone and a flushing liquid channel in the stylet guide housing having an exit port positioned to direct flushing liquid issuing therefrom across the end of a fiber optic device when positioned in the viewing zone. The optical viewing means can comprise a viewing window positioned in the stylet guide housing for viewing the stylet when it is directed outward from its respective stylet port. The optical viewing means can include a fiber optic channel in the stylet guide housing for receiving the a fiber optic viewing device and aligning the viewing end thereof with the viewing window. Windowed devices can include a flushing liquid channel in the stylet guide housing having an exit port positioned to direct flushing liquid issuing therefrom across a surface of the viewing window.

30 Claims, 15 Drawing Sheets

OTHER PUBLICATIONS

Graverson, et al., "Transurethral incisions of the prostate under local anaesthesia in high–risk patients: a pilot study," (1987) Abstract, HealthGate Home Page, p. P000115.

Miller, et al., "Integrated cystoscope: first rigid multipurpose operating cystoscope for local anesthetic endoscopy," (1989) Abstract, HealthGate Home Page, p. P000116.

Orandi, "Urological endoscopic surgery under local anesthesia: a cost–reducing idea," (1984) Abstract, HealthGate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.GOV, U.S. Patent No. 3,991,770, pp. P000119–P000120.

R. Auhll, "The Use of the Resectoscope in Gynecology," (Oct. 1990) Biomedical Business International, pp. 91–99.

L. Geddes, "A Short History of the Electrical Stimulation of Excitable Tissue Including Electrotherapeutic Applications," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 2., pp. P000191–P000195.

T. Kirwin, "The Treatment of Prostatic Hypertrophy by a New 'Shrinkage 'Method ," (Aug. 1934) J. Urology, pp. 481–494.

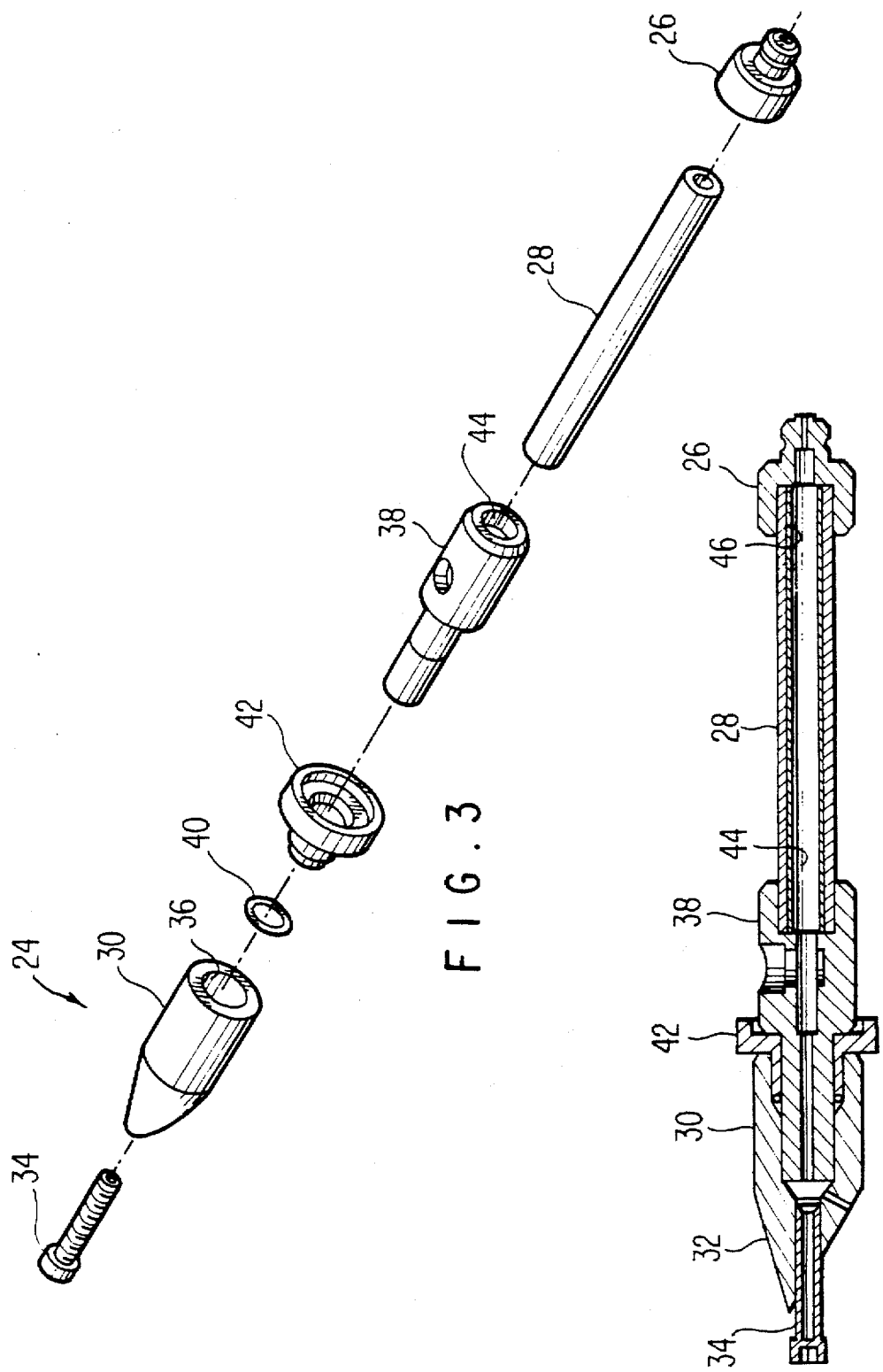

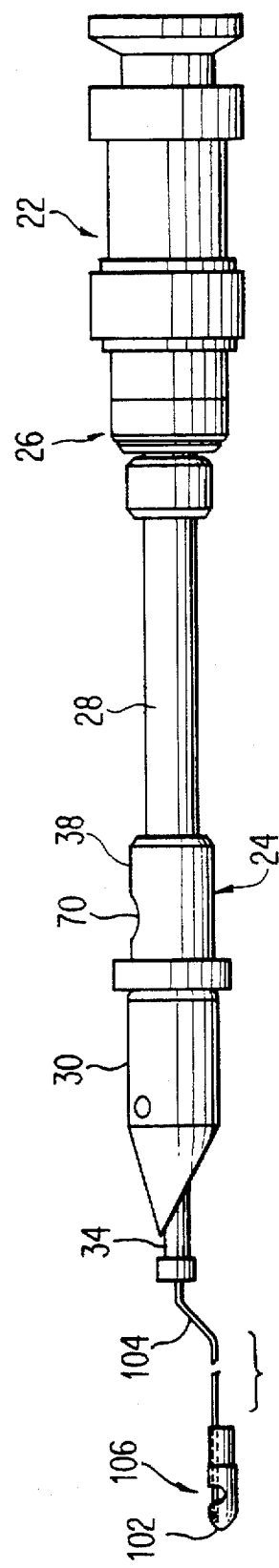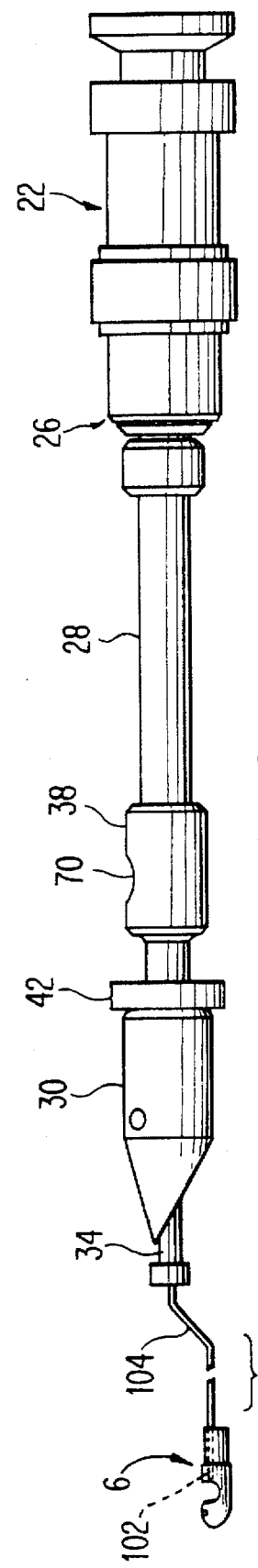

F I G . 11
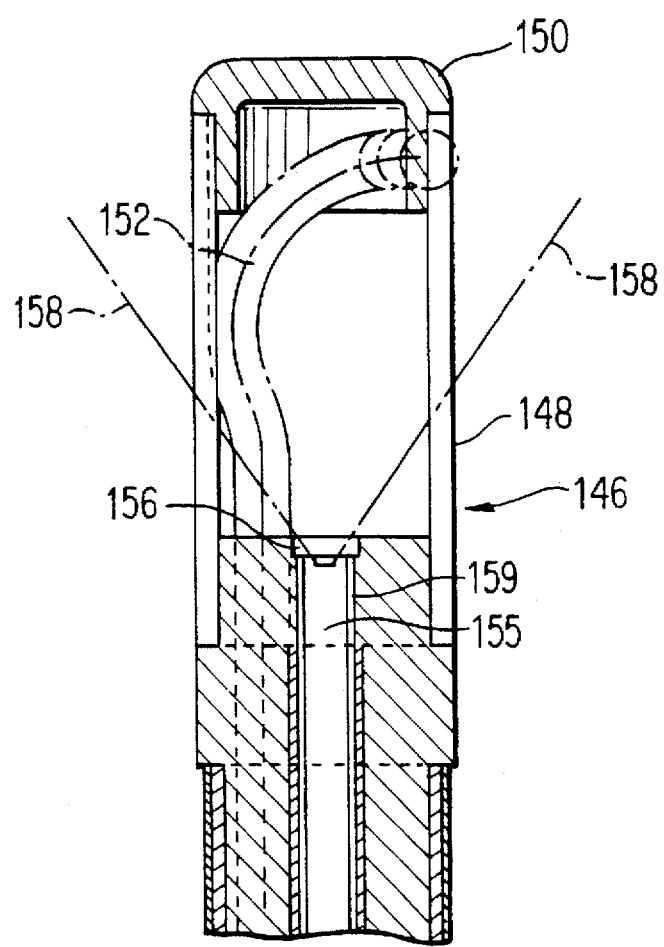

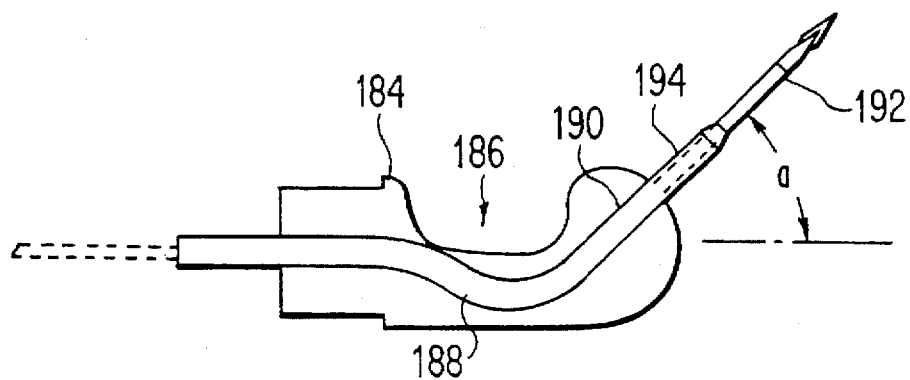
F I G . 15
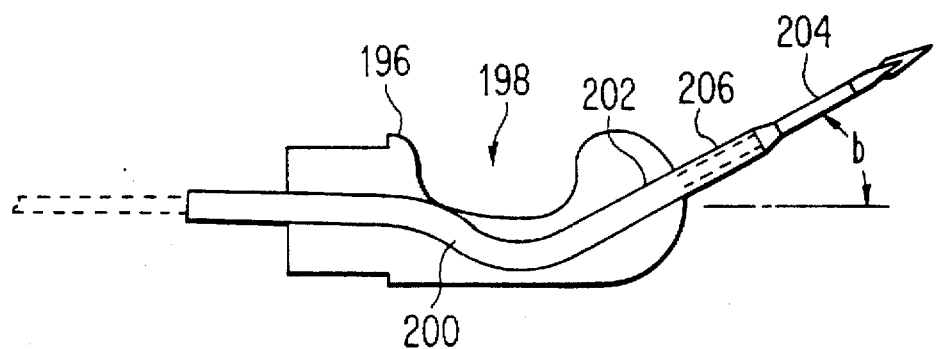
F I G . 16
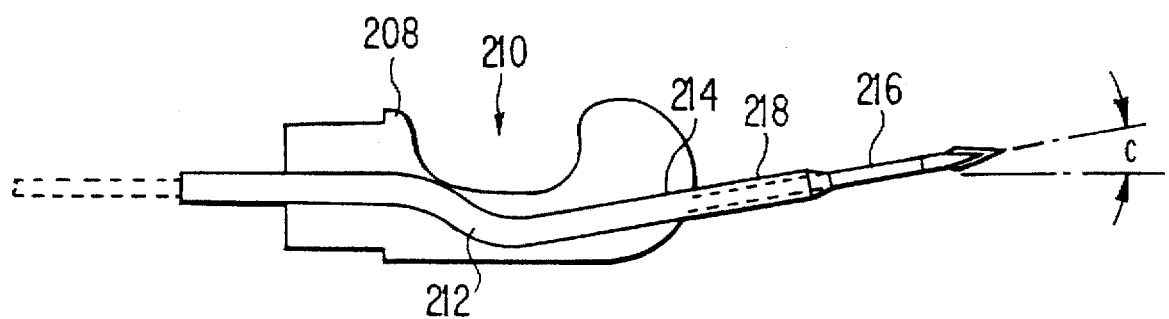
F I G . 17

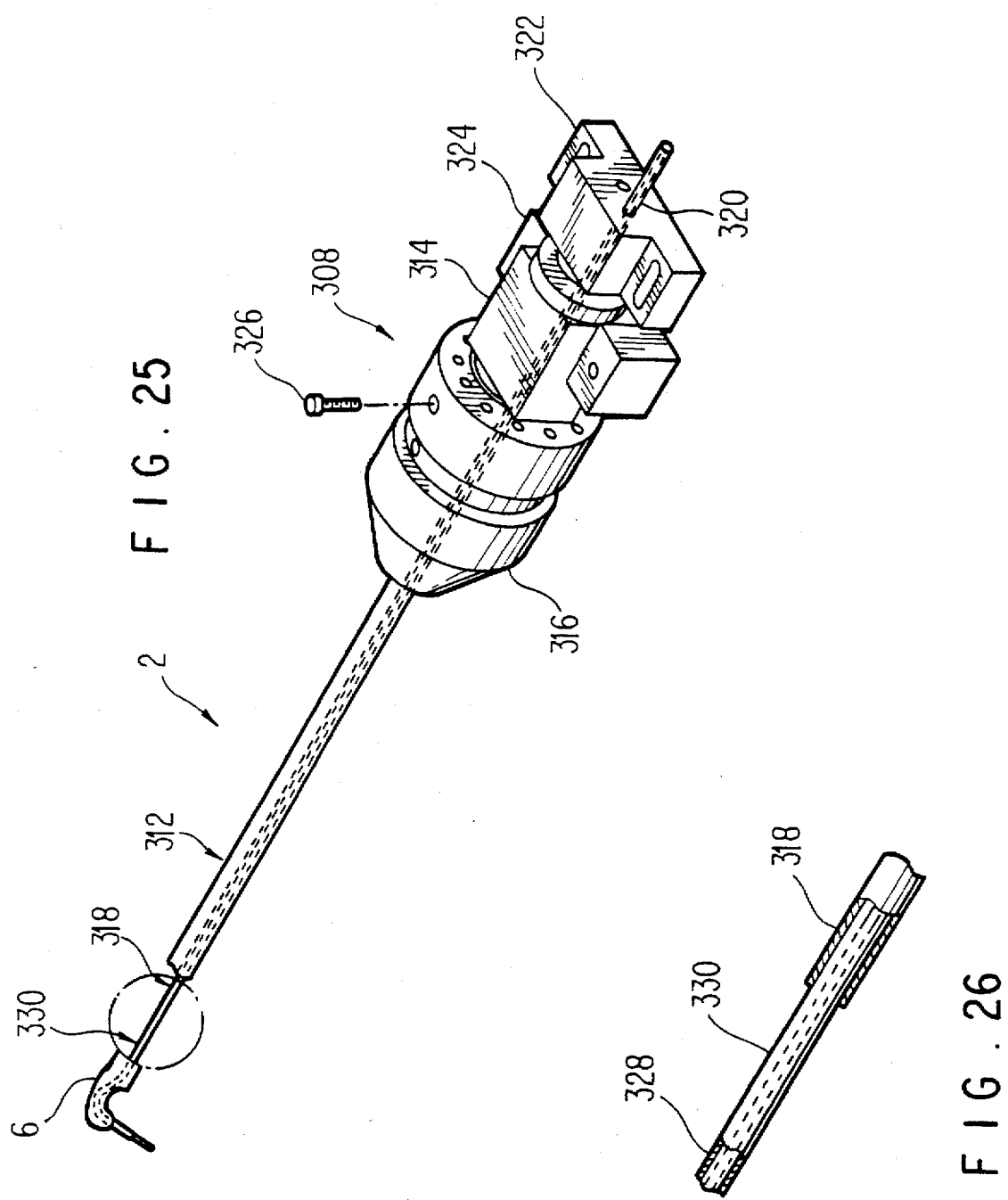

5,749,846

MEDICAL PROBE DEVICE WITH OPTICAL VIEWING CAPABILITY

RELATIONSHIP TO COPENDING APPLICATION

This application is a continuation of U.S. application Ser. No. 08/062,364, filed May 13, 1993, now U.S. Pat. No. 5,435,805 which is a continuation-in-part of application Ser. No. 07/929,638 filed Aug. 12, 1992 and now abandoned; and a continuation in part of Ser. No. 08/012,370 filed Feb. 2, 1993, and now U.S. Pat. No. 5,370,675. The entire contents of the above applications are hereby incorporated by reference.

FIELD OF THE INVENTION

This invention is directed to a unique device and method for penetrating body tissues for medical purposes such as tissue ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port in the side of the catheter through surrounding tissue to the tissue targeted for medical intervention.

In particular, this invention is directed to a medical probe device provided with an optical viewing capability for precise positioning of the treatment device.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown by the incidence of BPH in 50 percent of men over 50 years of age and increases in incidence to over 75 percent in men over 80 years of age. Symptoms of urinary obstruction occur most frequently between the ages of 65 and 70 when approximately 65 percent of men in this age group have prostatic enlargement.

Currently there is no nonsurgical method for treating BPH which has proven to be effective. In addition, the surgical procedures available are not totally satisfactory. Currently, patients suffering from the obstructive symptoms of this disease are provided with few options: continue to cope with the symptoms (i.e., conservative management), submit to drug therapy at early stages, or submit to surgical intervention. More than 430,000 patients per year in the United States undergo surgery for removal of prostatic tissue. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.), which is not without significant consequences. Also, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture, and the tissue is separated.

Ablation of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses in organs such as the prostate, and glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular ablation process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid supply catheter opening at the specific target tissue.

In addition to ultrasound positioning capabilities, it is desirable to provide the operator with the ability to optically examine the location and surfaces of the duct or other passageway in which the catheter is positioned for treatment, to locate abnormalities and more importantly, to precisely position the catheter tip. Retention of fertility after BPH treatment, for example, requires that the seminal vesical openings into the urethra remain undamaged. Precise location of these openings and the positioning of the catheter tip to avoid damage to them requires simultaneous optical viewing of the urethra surface and the catheter tip.

OBJECTS AND SUMMARY OF THE INVENTION

It is one object of this invention to provide a device with an optical viewing capability for penetrating tissue, through intervening tissues to the precise target tissue selected for a medical action such as tissue ablation and/or substance delivery, limiting this activity to the precise preselected site, thereby minimizing the trauma and achieving a greater medical benefit.

Another object of this invention is to provide a device with optical viewing capability for precise placement of the device which delivers the therapeutic energy into targeted tissues while minimizing effects on its surrounding tissue.

A still further object of this invention is to provide a device and method for introducing fluid treatment agents such as flowable liquids or gases, with greater precision and ease to a specific location in the body.

A further object of this invention is to provide a thermal ablation device which provides more control over the physical placement of the stylet and over the parameters of the tissue ablation process.

In summary, the device of this invention is a medical probe device comprising a catheter having a stylet guide housing with at least one stylet port in a side thereof and stylet guide means for directing a flexible stylet outward through at least one stylet port and through intervening tissue to targeted tissues. The stylet guide housing has an optical viewing means positioned for viewing the stylet which includes a fiber optic channel means for receiving a fiber optic viewing device. The fiber optic channel means can include a guide port means for directing axial or longitudinal movement of a fiber optic device with respect to the stylet guide means in a viewing zone.

The device preferably includes a flushing liquid channel in the stylet guide housing having an exit port positioned to direct flushing liquid issuing therefrom across the end of a fiber optic device when positioned in the viewing zone.

The optical viewing means can optionally comprise a viewing window positioned in the stylet guide housing for viewing the stylet when it is directed outward from its respective stylet port. The optical viewing means can include a fiber optic channel in the stylet guide housing for receiving the a fiber optic viewing device and aligning the viewing end thereof with the viewing window. Windowed devices can include a flushing liquid channel in the stylet guide housing having an exit port positioned to direct flushing liquid issuing therefrom across a surface of the viewing window.

The device preferably includes at least one flushing liquid return lumen extending to the stylet guide housing.

In the preferred embodiment of this invention, the stylet comprises an electrical conductor enclosed within a non-conductive sleeve, the electrical conductor being a radiofrequency electrode.

In one embodiment, the stylet guide housing has a tip portion in which the stylet guide means is positioned and the fiber optic channel means terminates at a position behind the tip, whereby surfaces adjacent the tip portion can be viewed. This can include a transverse depression positioned between said position behind the tip and the tip which opens the viewing field of a fiber optic when positioned in the fiber optic channel. In some embodiments, the tip defines an fiber optic passageway means for axial or longitudinal extension of the fiber optic to the end of the style guide housing. The passageway means can be a longitudinal hole extending to the end of the housing. Alternatively, the fiber optic passageway means is an axial or longitudinal depression extending to the terminal surface of the tip and the transverse depression, to open the axial viewing field of a fiber optic when positioned in the fiber optic channel.

Alternatively, the stylet guide housing can include a window extending to said tip for the viewing field of a fiber optic when positioned in the fiber optic channel.

The invention includes the medical probe device in combination with a fiber optic viewing assembly comprising an eyepiece, a fiber optic, a focal lens, and means for adjusting the axial or longitudinal position of the focal lens with respect to the fiber optic.

Some embodiments include a stylet positioned in at least one of said stylet guide means, the stylet axis forming an angle of from 10° to 90° with the central axis of the stylet guide housing. In one configuration, the stylet guide housing has an open end with a curved lip which maintains the stylet axis at said angle.

The device can have a system to maintain precise positioning of the stylet tip comprising a catheter having a stylet guide housing at its distal end and a tension and torque tube assembly at the proximal end thereof. The stylet guide housing has at least one stylet port in a side thereof and stylet guide means for directing a flexible stylet outward through a stylet port and through intervening tissue to targeted tissues. The tension and torque assembly can include a twist control knob and torque coupler, an outer torque tube attached to the torque coupler and extending from the torque coupler through the twist control knob to the stylet guide housing. The tension and torque tube assembly includes an adjusting block means, an non-extendable tension tube having its proximal end secured to the adjusting block and its distal end secured to the stylet guide housing, the non-extendable tension tube being enclosed within the torque tube and enclosing at least one stylet.

BRIEF DESCRIPTION OF THE DRAWINGS

FIG. 2 is a cross-sectional view of the optics connecting assembly of the embodiment of FIG. 1.

FIG. 3 is an exploded, isometric view of the optics connecting assembly of the embodiment of FIG. 1.

FIG. 6 is a cross-sectional view of the fiber optic viewing accessory shown in FIG. 1 with the fiber optic viewer retracted.

FIG. 7 is a cross-sectional view of the fiber optic viewing accessory shown in FIG. 1 with the fiber optic viewer extended.

FIG. 11 is a cross-sectional view of an alternative catheter tip and stylet guide housing embodiment with a fiber optic viewing window permitting a view of the stylet deployment.

FIG. 15 is a cross-sectional side view of an alternative 45° stylet guide housing of this invention.

FIG. 16 is a cross-sectional side view of an alternative 30° stylet guide housing of this invention.

FIG. 17 is a cross-sectional side view of an alternative 10° stylet guide housing of this invention.

FIG. 25 is an isometric view of the adjuster block and tension tube assembly of the RF ablation catheter shown in FIG. 24.

FIG. 26 is a detailed view "A" of the tension tube connections shown in FIG. 25.

DETAILED DESCRIPTION OF THE INVENTION

Figure 1:
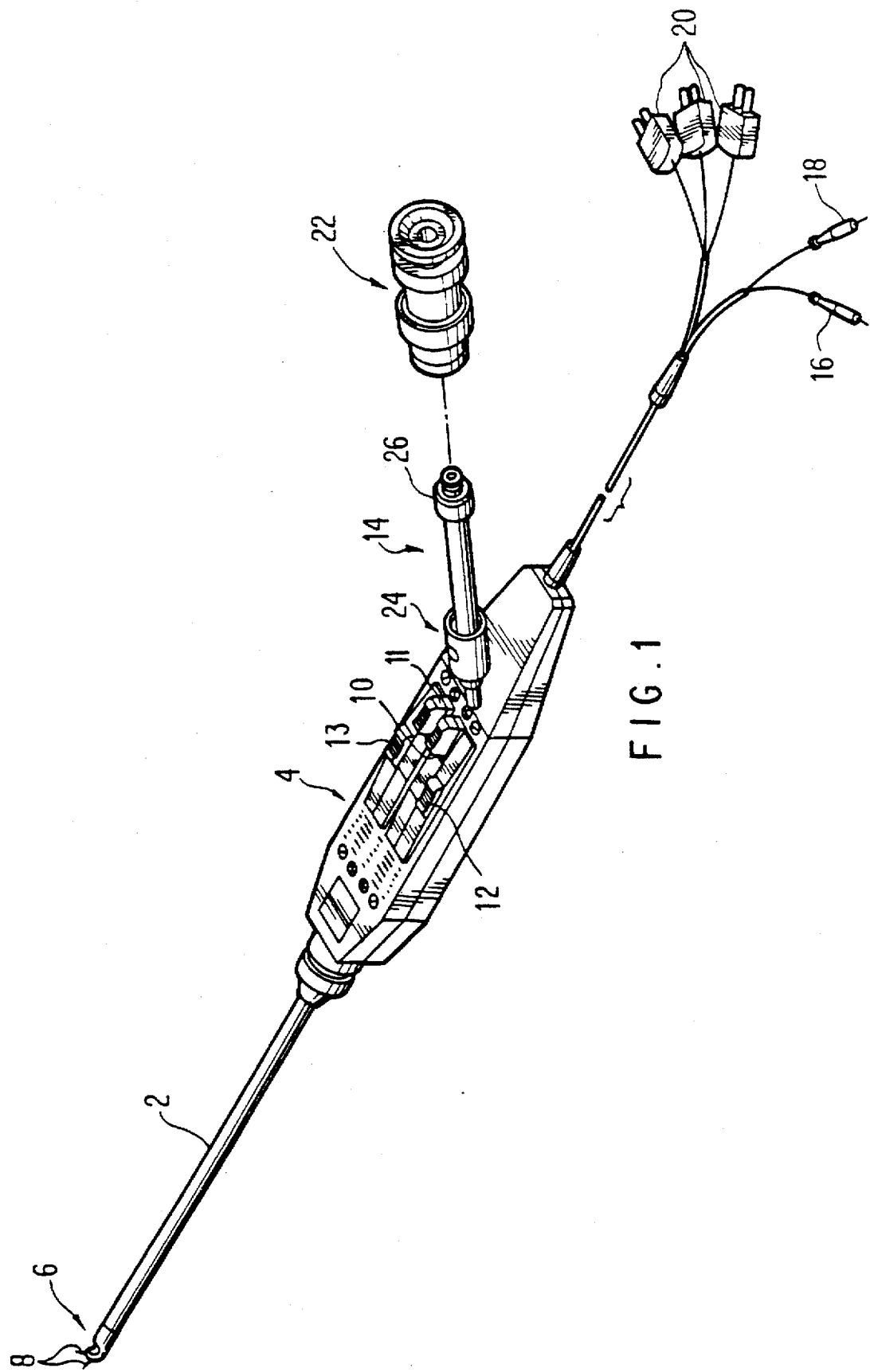
FIG. 1 is an isometric view of an RF ablation catheter embodiment of this invention with an fiber optic viewing accessory.

The device of this invention provides a precise controlled positioning of a treatment stylet in a tissue targeted for treatment, ablation or sampling from a catheter positioned in the vicinity of targeted tissues.

The term "stylet" as used hereinafter is defined to include both solid and hollow probes which are adapted to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site.

The stylet can be designed to provide a variety of medically desired treatments of a selected tissue. As a radiofrequency electrode or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue ablation with electrodes positioned within the urethra exposes the urethral wall to destructive temperatures. To avoid this, temperature settings required to protect the urethra must be so low that the treatment time required to produce any useful effect is unduly extended, e.g. up to three hours of energy application.

One embodiment of the device of this invention uses the urethra to access the prostate and positions RF electrode stylets directly into the tissues or nodules to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablation is confined to the tissues targeted for ablation, namely those causing the mechanical constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of an RF ablation catheter embodiment of this invention with a fiber optic viewing accessory. The flexible catheter 2, attached to handle 4, has a terminal stylet guide 6 with two stylets 8. The handle has stylet electrode tabs 10 and 11 and sleeve tabs 12 and 13 as will be described in greater detail hereinafter. The handle 4 is also connected to an optical viewing assembly 14 and RF power connector 16, transponder connector 18 and thermocouple connectors 20. The portions of the catheter 2 leading from the handle 4 to the stylet guide tip 6 can optionally have a graduated stiffness. For example, the catheter can be designed to be more stiff near the handle and more flexible near the tip, or any other stiffness profiles. The catheter can be constructed of an inner slotted stainless steel tube with outer flexible sleeve such as is described in U.S. Pat. No. 5,322,064, the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

FIG. 2 is a cross-sectional view and FIG. 3 is an exploded, isometric view of the optics connecting assembly of the embodiment of FIG. 1. The lens connector assembly 24 comprises receptor housing 30 having a threaded bore 32. Engagement of the threaded bore 32 with the threaded tubular housing connector 34 secures the optical assembly to the handle 4 (FIG. 1). An interior cavity 36 of the receptor housing 30 receives the distal end of the fiber optic control housing 38, and the opposed surfaces thereof are sealed by O-ring 40 and flange 42 to prevent escape of flushing fluid. One end of the flexible tubing 28 engages cylindrical receptor 44 of the fiber optic control housing 38, and the other end engages a cylindrical receptor 46 in the male quick release member 26.

Figure 4:
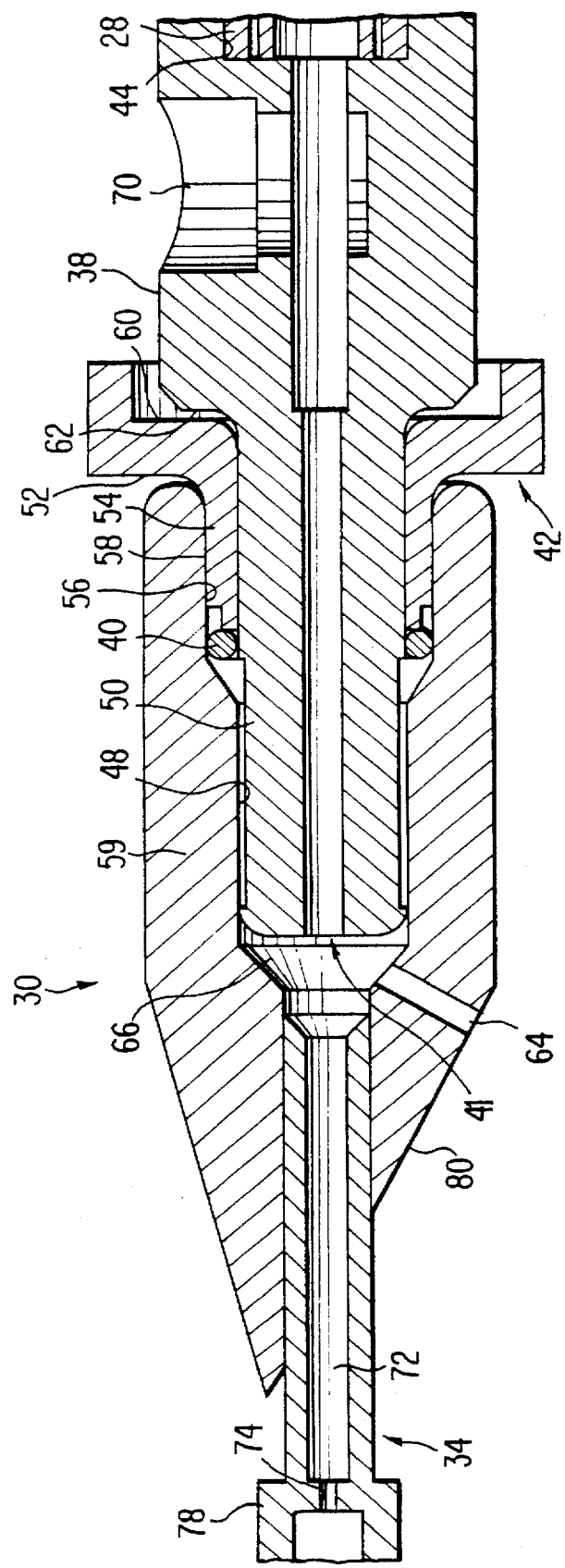
FIG. 4 is an enlarged cross-sectional view of the fiber optic extension system of the embodiment shown in FIGS. 1-3.

FIG. 4 is an enlarged cross-sectional view of the fiber optic extension system of the embodiment shown in FIGS. 1–3. Axial or longitudinal adjustment of the fiber optic control housing 38 effects axial or longitudinal movement of the fiber optic in the stylet guide housing as will be described in greater detail hereinafter. This axial or longitudinal adjustment is effected by the relative movement between inner surface 48 of housing 30 and the outer surface 50 of the distal end of the fiber optic control housing 38. Advancing movement of the fiber optic control housing 38 (leftward movement in this figure) is limited by the abutment of surface 52 of flange 42 with the opposing end surface of the receptor housing 30. The flange 42 has an annular distal sleeve terminus 54 which is held between respective cylindrical inner surface 56 of the receptor housing 30 and outer surface 58 of control housing 38. Its advancing movement is limited by abutment of surface 60 of the flange 42 and opposed abutment surface 62 of the control housing 38. Retracting movement of control housing 38 and the fiber optic attached thereto is limited by impingement of annular stop rim 59 against O-ring 40.

Flushing liquid to clean the viewing tip of the fiber optic is provided through flushing liquid supply bore 64 from a flushing liquid supply connector (not shown) and enters the cavity 66. Escape of the liquid from between the receptor housing 30 and the control housing 38 is prevented by the sealing engagement of the O-ring 40 with the surfaces opposed thereto and a seal (not shown) in opening 41. The liquid flows through channel 72 and opening 74, and then through a tubing (not shown) surrounding the fiber optic. Outlet port 70 receives a conventional fiber optic illumination light source connection.

The distal tip of the housing connector has an expanded diameter or flange 78 for connection with the handle 4. The receptor housing has a mounting surface 80 at a sloped angle with the axis thereof for engaging an opposed upper surface of handle 4 (FIG. 1).

Figure 5:
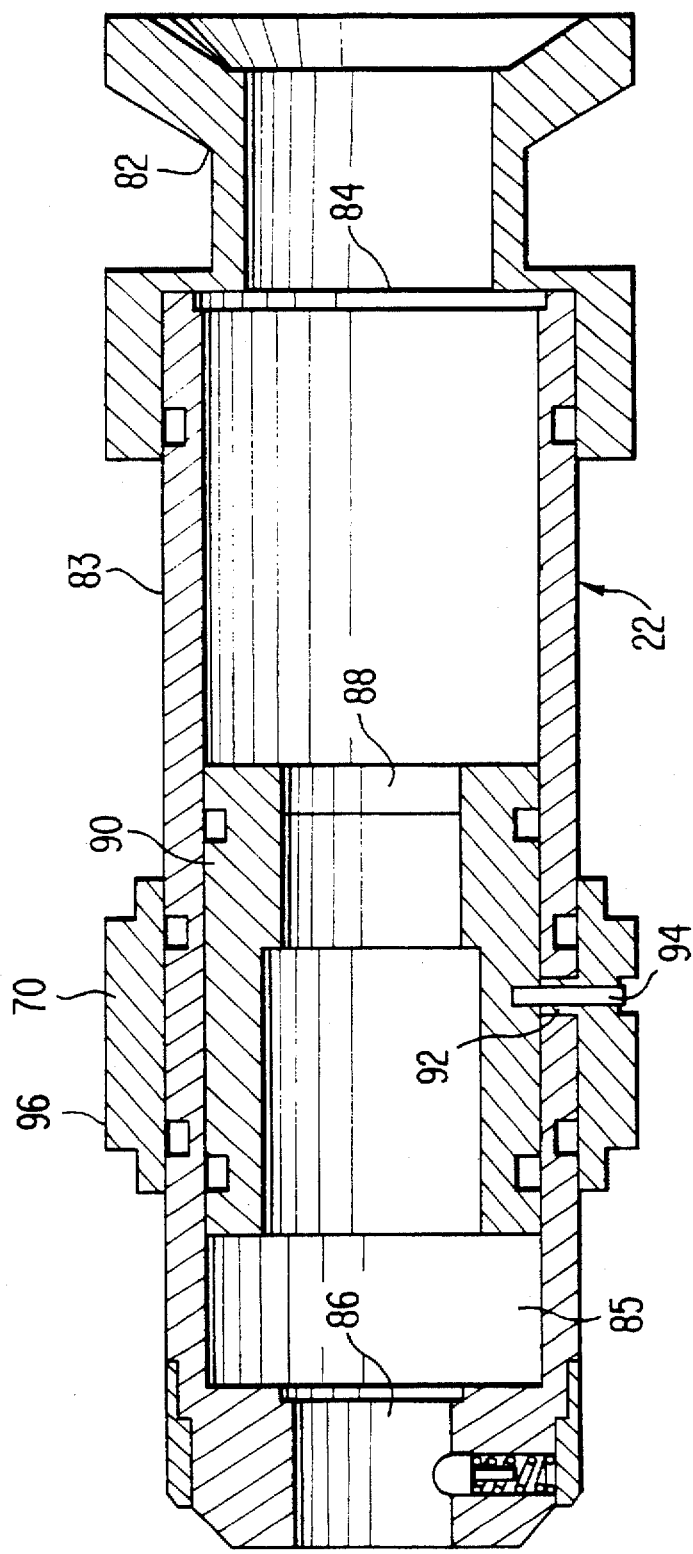
FIG. 5 is a cross-sectional view of the optics system of the embodiment shown in FIG. 1.

FIG. 5 is a cross-sectional view of the optics system of the embodiment shown in FIG. 1. The conventional focusing system 22 comprises an eyepiece 82 connected to the end of cylinder 83. Transparent window 84 is mounted in the proximal end. A quick disconnect junction 86 is positioned at the distal end of the cylinder 83. The proximal viewing end of the fiber optic (not shown) is mounted in the cavity 85.

The lens focusing system comprises a conventional convex lens 88 mounted in a lens support cylinder 90. A manual adjusting sleeve 96 is mounted for sliding movement about the cylinder 83. The adjusting sleeve 96 is attached to the lens support 90 by pin 94 which extends through slot 92. Slot 92 has the shape of a short portion of a helix so that rotation of sleeve 96 about the sleeve in the clockwise direction and counter-clockwise moves the lens toward or away from the fiber optic viewing end, respectively, to bring the image into focus for the viewer.

FIG. 6 is a cross-sectional view of the fiber optic viewing accessory shown in FIG. 1 with the fiber optic viewer retracted, and FIG. 7 is a cross-sectional view of the fiber optic viewing accessory shown in FIG. 2 with the fiber optic viewer extended. As the fiber optic control housing 38 is advanced by the operator into the receptor housing 30, the viewing tip 102 of fiber optic 104 is advanced outward through the stylet guide housing 6 toward the tip thereof from the position shown in FIG. 6 to the position shown in FIG. 7, enabling the operator to view the duct surfaces surrounding the housing 6 to determine the condition of these surfaces and locate the position of ducts such as the seminal ducts which are to be avoided in the treatment. The stylet housing tip 6 is moved to position it in the desired location by movement of the handle 4 and catheter 2 (FIG. 1). By retracting the fiber optic control housing 38 from the housing 30, the fiber optic viewing tip 102 is withdrawn to the surface of the stylet guide housing 6 as shown in FIG. 6 for viewing the surface through which the stylets 8 (FIG. 1) are to be extended.

Figure 8:
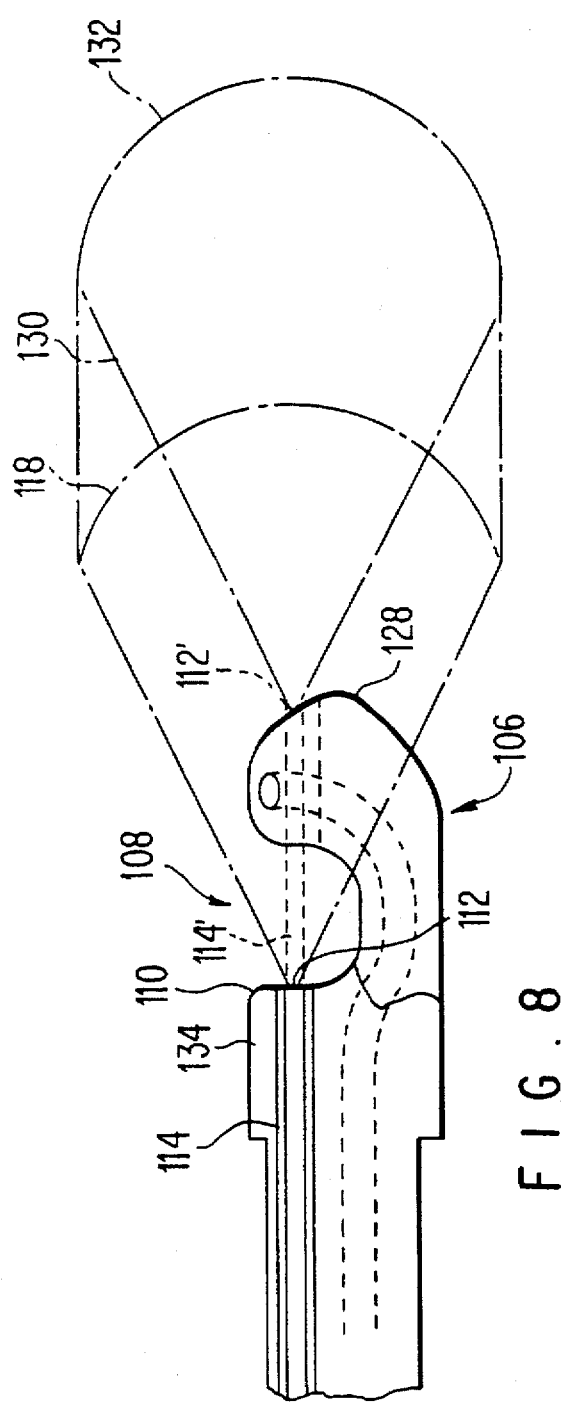
FIG. 8 is a fragmented cross-sectional view of a preferred catheter tip and stylet guide housing of this invention.

FIG. 8 is a fragmented cross-sectional view of a preferred catheter tip and stylet guide housing of this invention. The solid catheter tip 106 has a lateral depression or saddle 108 therein having a central axis approximately perpendicular to a plane through the central axis of the tip. The depression 108 has a proximal wall 110. The depression 108 can extend up to approximately half of the thickness of the housing, but at least sufficiently to unblock the viewing surface of the viewing tip 112 of the fiber optic 114. The fiber optic viewing tip 112, when positioned at the opening in wall 110, provides a field of view with lateral margins 116 and a terminal margin 118. This includes the path of stylets extended outward through ports 120.

Figure 9:
FIG. 9 a distal end view of the catheter tip and style guide housing shown in FIG. 8.

FIG. 9 is a distal end view of the catheter tip and style guide housing shown in FIG. 8. The proximal end of depression 108 is split to form two projections or ears 122 and 124 which define a longitudinal or axial or longitudinal groove or saddle 126 extending from the depression 108 to the terminal tip 128 of the catheter 106. Groove 126 opens the field of view for the viewing tip 112 when in the solid line position shown in FIG. 8 and permits extension of the fiber optic and its tip (as described with respect to FIGS. 4, 6 and 7) through the longitudinal groove to the dotted line positions 114' and 112'. In the latter position, the field of vision has side margins 130 and a terminal margin 132. This permits the operator to examine the inner duct surfaces ahead of the catheter tip. In an alternative embodiment, the grove 126 can be replaced with a hole in the end of the tip having a size and position to permit extension of the fiber optic 114 therethrough.

The fiber optic 114 is positioned in a passageway 134 which is sufficiently larger than the fiber optic to permit flow of flushing liquid around the fiber optic to the exit in wall 110. The flushing liquid flow clears debris from the viewing tip. The inner walls of the duct (not shown) surrounding the catheter tip 106 during use confine the liquid flow, so the liquid continues to pass over the fiber optic tip even when it has been advanced to the dotted line position. Return flushing liquid lumina 136 and 138 extend through wall 110 for constant removal of contaminated flushing liquid.

Figure 10:
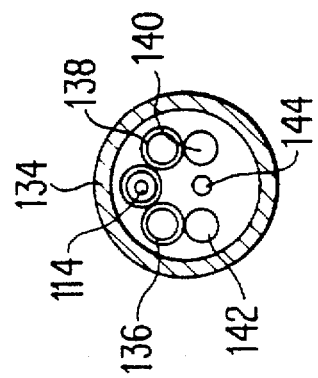
FIG. 10 is a proximal end view of the unassembled catheter tip and stylet guide housing shown in FIG. 8, showing the lumina for the components thereof.

FIG. 10 is a proximal end view of the unassembled catheter tip and stylet guide housing shown in FIG. 8, showing the lumina for the components thereof. The stylets are advanced and retracted through stylet lumina 140 and 142 to the stylet ports 120. The fiber optic is advanced and retracted through fiber optic lumen 134. The contaminated flushing fluid is removed through flushing fluid return lumina 136 and 138. Temperature sensor lumen 144 is used to house leads of a temperature sensor (not shown).

FIG. 11 is a cross-sectional view of a catheter tip and stylet guide housing embodiment with a cylindrical fiber optic viewing window permitting a view of the stylet deployment. In this view, the catheter end 146 includes a short cylindrical, transparent window 148 and tip cap 150.

Stylet guide tubing 152 extends through the enclosure defined by the window 148 to ports (not shown). The catheter end 146 has a lumen 154 in which a fiber optic 155 can be positioned and a transparent plate 156 for sealing the end of the lumen 154. The margins 158 of the view through the plate 156 provide a wide 360° view of the inside surface of a surrounding duct and the extended stylets.

Figure 12:
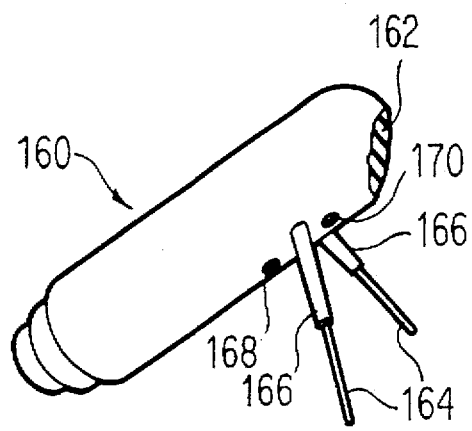
FIG. 12 is a isometric view of a further alternative catheter tip and stylet guide housing embodiment with a fiber optic viewing window in the end thereof.

FIG. 12 is an isometric view of a catheter tip and stylet guide housing embodiment with a fiber optic viewing window in the end thereof. This stylized view shows a catheter tip 160 with an optic viewing window 162 in the tip thereof. It has stylets extending through outlet ports therein, each stylet comprising an antenna 164 surrounded by an insulating sleeve 166. Temperature sensors 168 and 170 monitor the temperature in the duct wall surrounding the catheter. In this embodiment, the inside wall of the duct can be examined as the catheter is advanced to the desired position.

Figure 13:
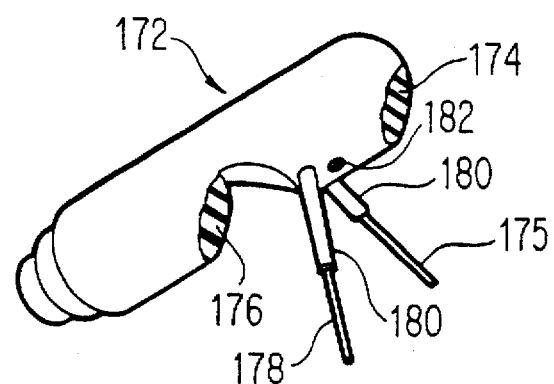
FIG. 13 is a isometric view of a still further alternative catheter tip and stylet guide housing embodiment with two fiber optic viewing windows, one at the end of the housing and the other rearward of the stylets.

FIG. 13 is a isometric view of a catheter tip and stylet guide housing embodiment with two fiber optic viewing windows, one at the end of the housing and the other rearward of the stylets. This stylized view shows a catheter tip 172 with two optic viewing windows 174 and 176 therein, and stylets extended through outlet ports therein, each stylet comprising an antenna 178 surrounded by an insulating sleeve 180. A temperature sensor 182 monitors the temperature in the duct wall surrounding the catheter. In this embodiment, two windows are provided, accommodating two fiber optics or two positions for a single fiber optic. Window 174 provides a view of the surrounding as the catheter is advanced to the desired position. Window 176 provides a view of the duct wall in the vicinity of the stylets.

Figure 14:
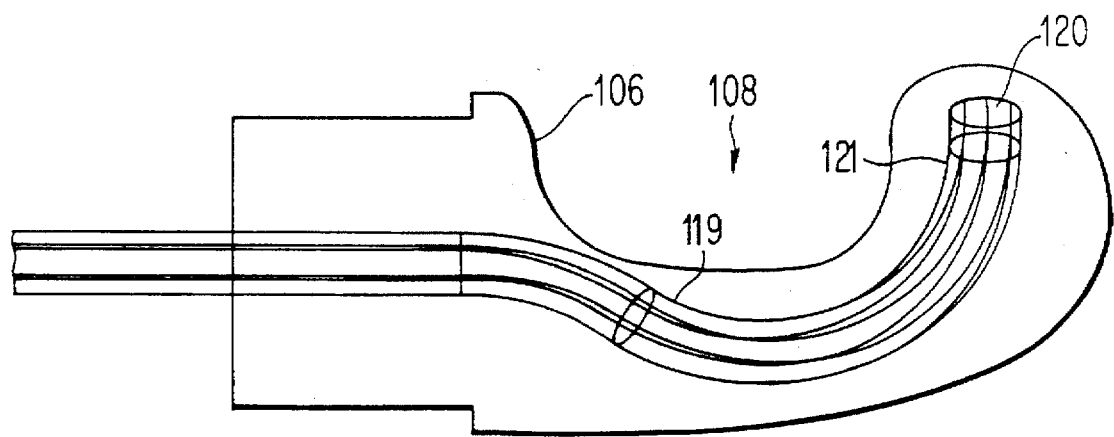
FIG. 14 is cross-sectional side view of an alternative 90° stylet guide housing shown in FIG. 8 with the stylet omitted.

FIG. 14 is a cross-sectional side view of an alternative 90° stylet guide housing shown in FIG. 8 with the stylet omitted. The solid catheter tip 106 has a curved guide channel 119 leading to port 120 through which the stylet is to be guided. Terminal portion 121 of the channel 119 has an orientation of 90° to the central axis of the housing.

FIG. 15 is a cross-sectional side view of an alternative 45° stylet guide housing of this invention. In this embodiment, the solid catheter tip 184 with lateral depression 186 has a curved channel 188, the terminal portion 190 thereof having an axis which forms an angle "a" with the central axis of the catheter tip. This deploys the antenna 192 and insulating sleeve 194 at an angle "a" in a plane through the central axis of the catheter tip. In this embodiment, angle "a" is preferably about 45°.

FIG. 16 is a cross-sectional side view of an alternative 30° stylet guide housing of this invention. In this embodiment, the solid catheter tip 196 with lateral depression 198 has a curved channel 200, the terminal portion 202 thereof having an axis which forms an angle "b" with the central axis of the catheter tip. This deploys the antenna 204 and insulating sleeve 206 at an angle "b" in a plane through the central axis of the catheter tip. In this embodiment, angle "b" is preferably about 30°.

FIG. 17 is a cross-sectional side view of an alternative 10° stylet guide housing of this invention. In this embodiment, the solid catheter tip 208 with lateral depression 210 has a curved channel 212, the terminal portion 214 thereof having an axis which forms an angle "c" with the central axis of the catheter tip. This deploys the antenna 216 and insulating sleeve 218 at an angle "c" in a plane through the central axis of the catheter tip. In this embodiment, angle "c" is preferably about 10°.

Figure 18:
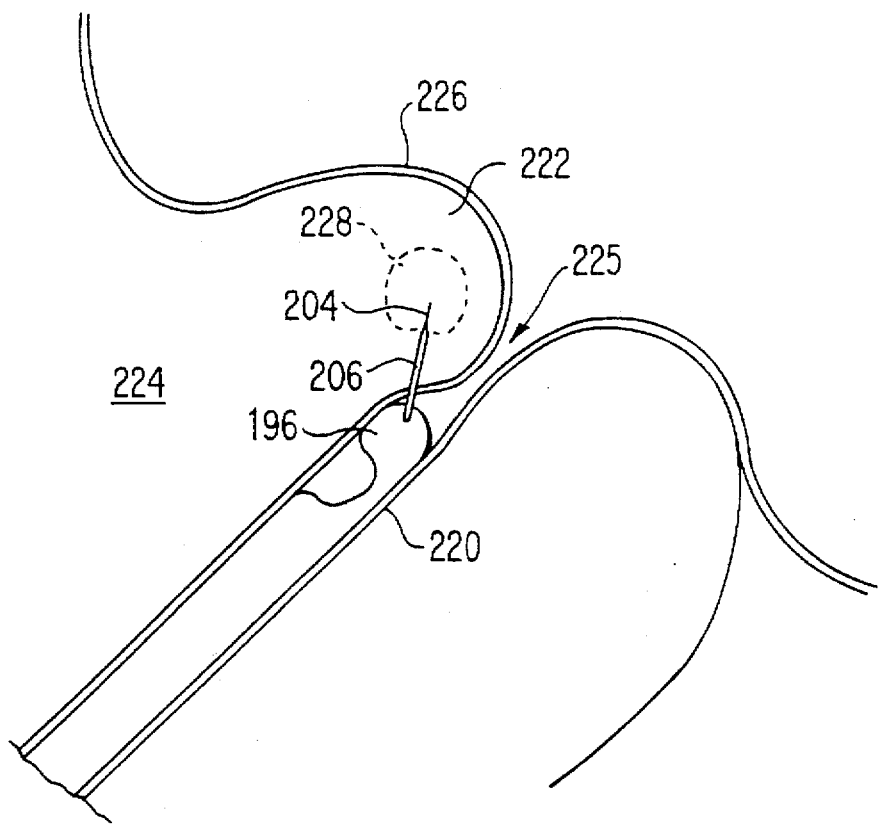
FIG. 18 is a schematic view of a stylet deployment into a portion of a prostate protruding into the urinary bladder.

FIG. 18 is a schematic view of a stylet of FIG. 16 shown deployed to treat a portion of a prostate protruding into the urinary bladder. The solid catheter tip 196 is positioned at the end of the urethra 220. Cell proliferation in the upper end 222 of the prostate 224 has caused it to protrude into space normally occupied by the urinary bladder, pushing a portion of the bladder wall 226 into the cavity and forming a restriction 225 beyond the end of the urethra. The stylet sleeve 206 and electrode 204 are extended at an angle of about 30° through the urethral wall into a portion of the protruded prostate, and RF current is applied to form the lesion 228. This will reduce the protruded prostate, promoting its retraction from the urethral wall and opening the restriction of the outlet end of the urethra. The catheter having a desired angle can be selected from those having angles "a", "b" or "c" shown in FIGS. 15–17 to precisely orient the stylet and effect precise penetration of prostate tissue which extends beyond the end of the urethra, for example.

Figure 19:
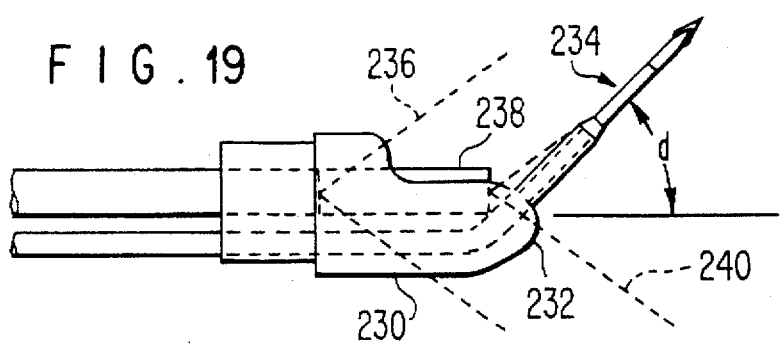
FIG. 19 is a side view of a 45° shovel nose stylet guide of this invention.

FIG. 19 is a side view of a 45° shovel nose stylet guide of this invention. In this embodiment, the catheter tip 230 has the shape of a shovel or scoop, the extended lip 232 of which guides the stylet 234 in a desired angle "d". This configuration opens the upper viewing field 236 of the fiber optic 238 in the unextended position and permits an unobstructed viewing field 240 in the fully extended position. In this embodiment, the angle "d" is about 45°.

Figure 20:
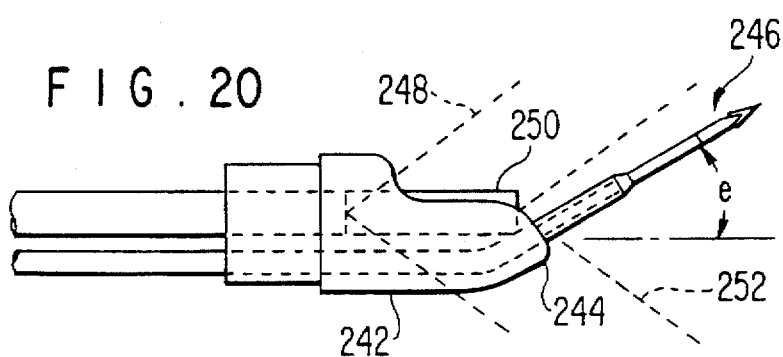
FIG. 20 is a side view of a 30° shovel nose stylet guide of this invention.

FIG. 20 is a side view of a 30° shovel nose stylet guide of this invention. In this embodiment, the catheter tip 242 has the shape of a shovel or scoop, the extended lip 244 of which guides the stylet 246 in a desired angle "e". This configuration opens the upper viewing field 248 of the fiber optic 250 in the unextended position and permits an unobstructed viewing field 252 in the fully extended position. In this embodiment, the angle "e" is about 30°.

Figure 21:
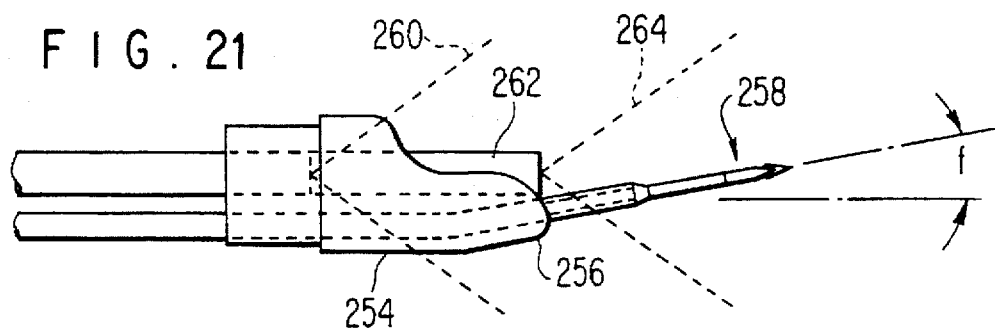
FIG. 21 is a side view of a 10° shovel nose stylet guide of this invention.

FIG. 21 is a side view of a 10° shovel nose stylet guide of this invention. In this embodiment, the catheter tip 254 has the shape of a shovel or scoop, the extended lip 256 of which guides the stylet 258 in a desired angle "f". This configuration opens the upper viewing field 260 of the fiber optic 262 in the unextended position and permits an unobstructed viewing field 264 in the fully extended position. In this embodiment, the angle "f" is about 10°.

Figure 22:
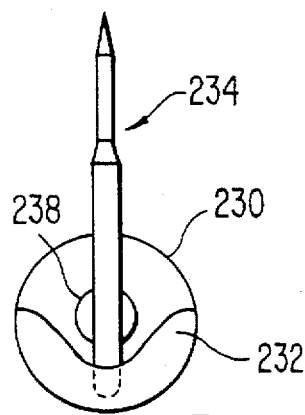
FIG. 22 is an end view of a shovel nose stylet guide of FIG. 19 for a single stylet.

FIG. 22 is an end view of a shovel nose stylet guide of FIG. 19 for a single stylet 234.

Figure 23:
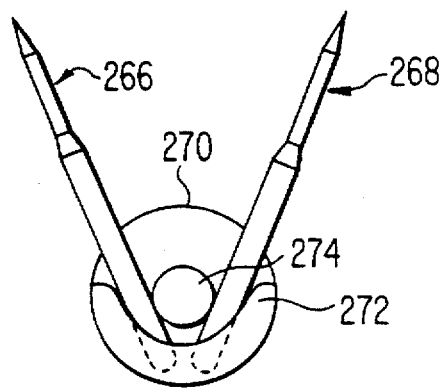
FIG. 23 is an end view of a shovel nose stylet guide of FIG. 19 for two stylets.

FIG. 23 is an end view of an alternative embodiment of a shovel nose stylet guide for two stylets 266 and 268, the stylet guide tip 270 having a shovel lip 272 and fiber optic 274.

Figure 24:
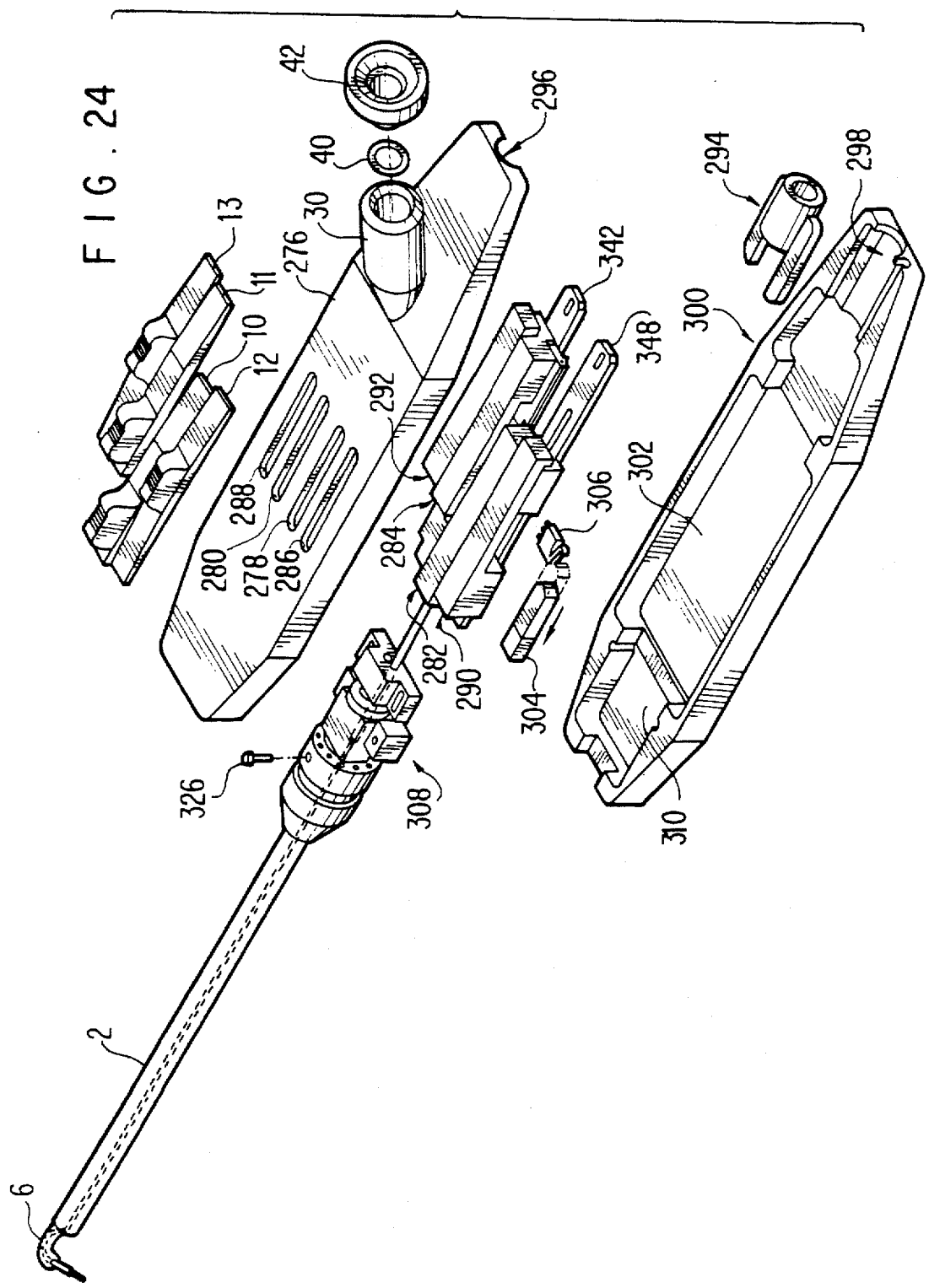
FIG. 24 is an exploded view of the RF ablation catheter shown in FIG. 1.

FIG. 24 is an exploded view of the RF ablation catheter assembly shown in FIG. 1. The upper handle plate 276 has two central slots 278 and 280 through which the electrode control slides 11 are attached to respective left electrode slide block 282 and right electrode slide block 284. Sleeve control slides 12 and 13 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the respective upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the respective RF power circuits open until the respective sleeves are advanced to a position beyond the urethra wall and into the prostate to prevent direct exposure of the urethra to the energized RF electrodes. Extension of the sleeve 5 mm beyond the guide is usually sufficient to protect the urethra.

The tension-torque tube assembly 308 is mounted in the distal end of the housing in the receptor 310.

FIG. 25 is an isometric view of the adjuster block and tension tube assembly 308 of the RF ablation catheter shown in FIG. 24. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the stylet sleeve and electrode components when the torque tube 312 is flexed, a tension tube 318 having a fixed length and diameter smaller than the inner diameter of the torque tube 312 is provided. The distal end of the tension tube 318 is securely attached to the stylet guide 6, and the proximal end 320 is secured to the adjuster block 322, for example by an adhesive. The axial or longitudinal position of the adjuster block 322 can be adjusted to insure the stylets are initially positioned just inside the outlet ports in the stylet guide 6. Torque coupler 314 is mounted on the coupler block 324. Twist control knob stop pin 326 extends into a grove (not shown) and limits rotation of the control knob 316.

FIG. 26 is a detailed view "A" of the distal end tension tube connections of the tension tube shown in FIG. 25. The tension tube 318 is securely connected to the proximal end 328 of the stylet guide 6, for example by a length of shrink tubing 330.

Figure 27:
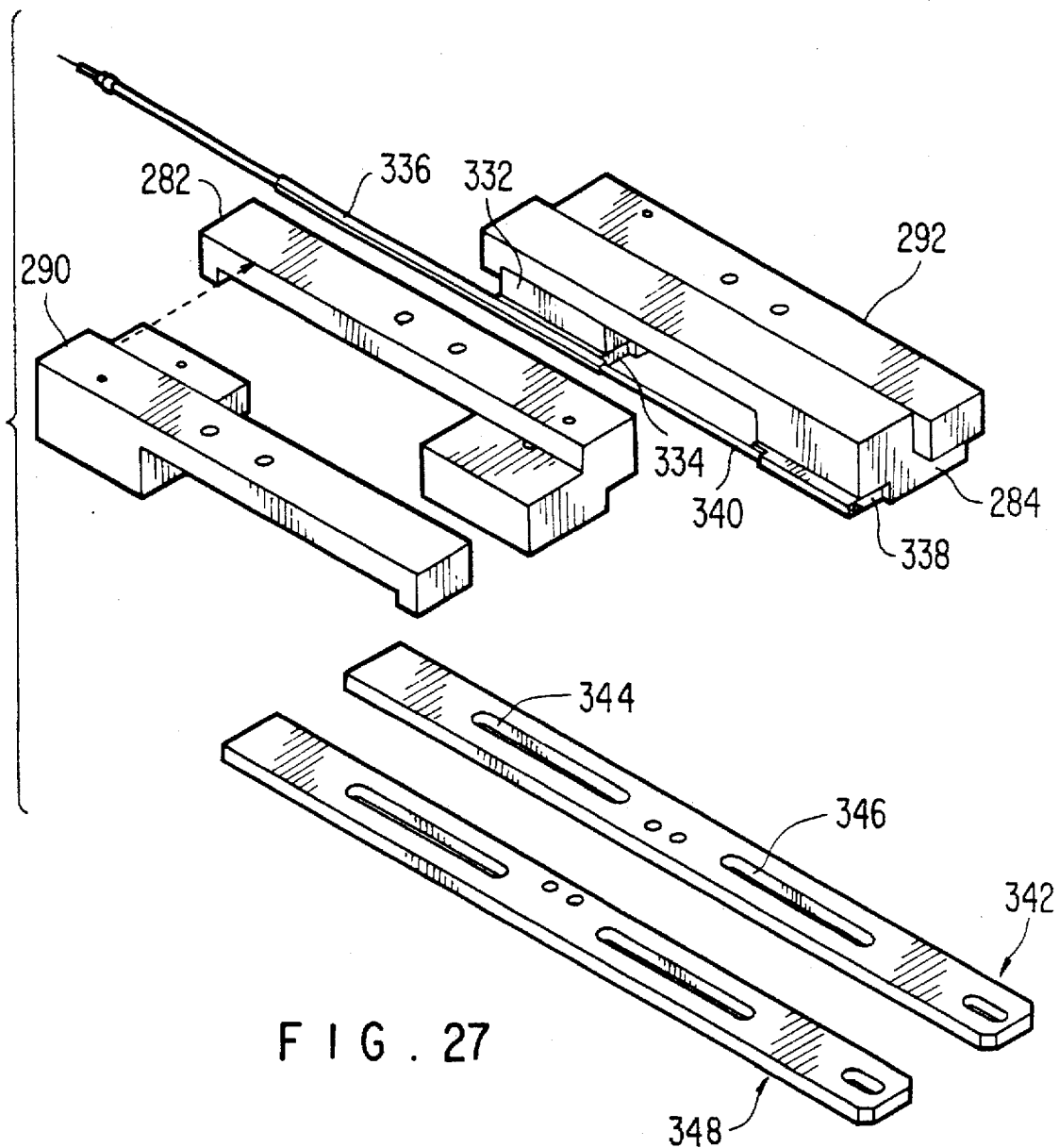
FIG. 27 is an exploded view of the sleeve and electrode slide block assembly of the embodiment shown in FIG. 24.

FIG. 27 is an exploded view of the sleeve and electrode slide block assembly of the embodiment shown in FIG. 24. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 344 and 346, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 348. The left sleeve and electrodes are not shown.

Figure 28:
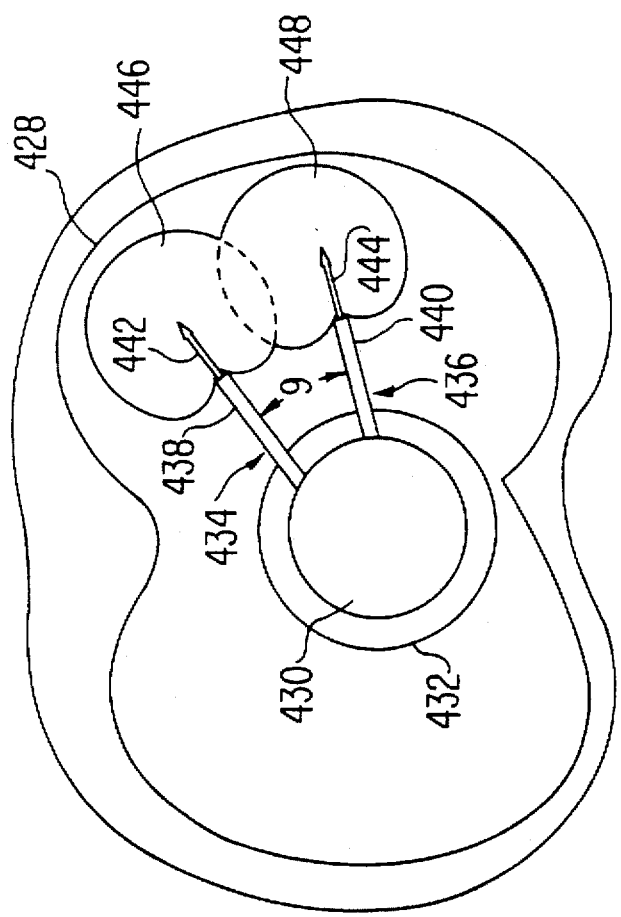
FIG. 28 is a schematic view of a deployment of two stylets in a prostate showing a stylet orientation for overlapping ablation zone method.

FIG. 28 is a schematic view of a deployment of two stylets in a prostate showing stylet orientation for overlapping ablation zone method of this invention. For purposes of illustration but not by way of limitation, the prostate has been selected for this explanation, and application of this method and assembly to other areas of the body are intended to be included.

The tissues to be treated for the treatment of BPH are located in the transition zone 428 of the prostate. A catheter of this invention 430 has been inserted up the urethra 432 to a position adjacent the prostate. Two stylets 434 and 436 have been passed through the urethra wall 432 through forward movement of tabs 12 and 13 (FIG. 1) and through surrounding tissue into targeted tissues. The non-conducting sleeves 438 and 440 have been retracted by rearward movement of sleeve tabs 12 and 13 to expose a portion of the respective electrical conductors 442 and 444 at the end of each stylet. The angle between the axes of the stylets in this embodiment, "f", is less than 180°, preferably less than 110°. For most overlapping ablations, angles of 15° to 90°, and more usually from 20° to 70° are most practical. A Grounding plate (not shown) is placed on the body exterior.

When electrodes 442 and 444 are supplied with RF current, the circuit from the electrodes to a grounding plate is closed. The current density flowing through the tissue passes through targeted tissues to be treated, creating lesions having the approximate cross-sectional shape of overlapping zones 446 and 448. The current density rapidly decreases as a function of distance, limiting the size of the lesions. In this manner, lesions can be caused to overlap to form a larger lesion, increasing the efficiency of the treatment. It will be readily apparent that these processes can be carried out concurrently, as described, or sequentially, and these variations are intended to be included in this invention.

Although preferred embodiments of the subject invention have been described in some detail, it is understood that obvious variations can be made without departing from the spirit and the scope of the invention as defined by the appended claims.

We claim:

1. A medical probe device for medical treatment of tissue of a prostate through a urethra defined by a urethral wall comprising a guide housing having proximal and distal extremities and having a passageway extending from the proximal extremity to the distal extremity, a stylet mounted in the guide housing, means carried by the distal extremity of the guide housing and in communication with said passageway for directing the stylet sidewise of the guide housing, the stylet including a flexible radio frequency electrode and an insulating sleeve coaxially mounted on the electrode, handle means coupled to the proximal extremity of the guide housing for introducing the distal extremity of the guide housing into the urethra into the vicinity of the prostate, said handle means including means secured to the stylet for advancing the stylet from the passageway of the guide housing to cause the radio frequency electrode and the insulating sleeve to penetrate the urethral wall and to extend into the tissue of the prostate with the insulating sleeve extending through the urethral wall and the radio frequency electrode having a predetermined length in the tissue of the prostate, means for supplying radio frequency energy to the radio frequency electrode to cause the temperature of the tissue of the prostate adjacent the predetermined length of the radio frequency electrode to be raised to cause destruction of cells in the tissue of the prostate and an optical viewing device positioned in the guide housing having a viewing field that extends forwardly and sidewardly of the guide housing to permit viewing of the radio frequency electrode and the insulating sleeve as they are deployed sidewise from the distal extremity of the guide housing.

2. A medical probe device as in claim 1 wherein the guide housing includes a channel receiving said optical viewing device and permitting longitudinal movement of the optical viewing device with respect to the guide housing to shift the viewing field.

3. A medical probe device as in claim 2 wherein the distal extremity of the guide housing has a tip and wherein the optical device viewing channel terminates at a position proximal of the tip.

4. A medical probe device as in claim 3 wherein said guide housing is provided with a transverse depression proximal of the tip and within the viewing field of the optical viewing device.

5. A medical probe device as in claim 3 wherein the distal extremity of the guide housing has a tip which includes a window extending across the viewing field.

6. A medical probe device as in claim 2 wherein the distal extremity of the guide housing has a tip and wherein the optical viewing device channel extends through the tip.

7. A medical probe device as in claim 6 wherein the distal extremity of the guide housing is provided with a transverse depression extending through and across the optical device viewing channel.

8. A medical probe device as in claim 1 wherein said guide housing includes a flushing liquid channel for directing a flushing liquid into the viewing field.

9. A medical probe device as in claim 8 wherein said guide housing includes at least one flushing liquid return lumen.

10. A medical probe device as in claim 1 wherein the optical viewing device comprises an eyepiece, a fiber optic, a focal lens and means for adjusting the longitudinal position of the focal lens with respect to the fiber optic.

11. A medical probe device for medical treatment of tissue of a prostate through a urethra defined by a urethral wall comprising a guide housing having proximal and distal extremities and having a passageway extending from the proximal extremity to the distal extremity, a stylet mounted in the guide housing, means carried by the distal extremity of the guide housing and in communication with said passageway for directing the stylet sidewise of the guide housing, the stylet including a flexible radio frequency electrode and a layer of insulating material coaxially mounted on the electrode, handle means coupled to the proximal extremity of the guide housing for introducing the distal extremity of the guide housing into the urethra into the vicinity of the prostate, said handle means including means secured to the stylet for advancing the stylet from the passageway of the guide housing to cause the radio frequency electrode and the layer of insulating material to penetrate the urethral wall and to extend into the tissue of the prostate with the layer of insulating material extending through the urethral wall and the radio frequency electrode having a length in the tissue of the prostate, means for supplying radio frequency energy to the radio frequency electrode to cause the temperature of the tissue of the prostate adjacent the length of the radio frequency electrode to be raised to cause destruction of cells in the tissue of the prostate and an optical viewing device positioned in the guide housing having a viewing field that extends forwardly and sidewardly of the guide housing to permit viewing of the radio frequency electrode and the layer of insulating material as they are deployed sidewise from the distal extremity of the guide housing.

12. A medical probe device as in claim 11 wherein the distal extremity of the guide housing has a tip and wherein the optical viewing device terminates at a position proximal of the tip.

13. A medical probe device as in claim 12 wherein the distal extremity of the guide housing is provided with a transverse depression proximal of the tip and within the viewing field of the optical viewing device.

14. A medical probe device as in claim 11 wherein the distal extremity of the guide housing has a tip which includes a window extending across the viewing field.

15. A medical probe device as in claim 11 wherein at least a portion of the distal extremity of the guide housing is transparent to permit the optical viewing device to view the radio frequency electrode and the layer of insulating material through the distal extremity of the guide housing as they are deployed sidewise from the distal extremity of the guide housing.

16. A medical probe device for medical treatment of tissue of a prostate through a urethra defined by a urethral wall comprising a guide housing having proximal and distal extremities and having a passageway extending from the proximal extremity to the distal extremity, a flexible radio frequency electrode mounted in the guide housing, means carried by the distal extremity of the guide housing and in communication with said passageway for directing the radio frequency electrode sidewise of the guide housing, handle means coupled to the proximal extremity of the guide housing for introducing the distal extremity of the guide housing into the urethra into the vicinity of the prostate, said handle means including means secured to the radio frequency electrode for advancing the radio frequency electrode from the passageway of the guide housing to cause the radio frequency electrode to penetrate the urethral wall and to extend into the tissue of the prostate, means for supplying radio frequency energy to the radio frequency electrode to cause the temperature of the tissue of the prostate adjacent the radio frequency electrode to be raised to cause destruction of cells in the tissue of the prostate and an optical viewing device positioned in the guide housing having a viewing field that extends forwardly and sidewardly of the guide housing to permit viewing of the radio frequency electrode as it is deployed sidewise from the distal extremity of the guide housing.

17. A medical probe device as in claim 16 together with a layer of insulating material coaxially mounted about at least a portion of the radio frequency electrode.

18. A medical probe device as in claim 16 wherein the radio frequency electrode is provided with a longitudinal lumen extending therethrough.

19. A medical probe device for use in a human body comprising an elongate member having proximal and distal extremities and having a passageway therein extending along a longitudinal axis from the proximal extremity to the distal extremity, an elongate needle mounted in the passageway and having proximal and distal extremities, handle means coupled to the proximal extremity of the elongate member for introducing the distal extremity of the elongate member into the body, means connected to the elongate needle for causing advancement of the elongate needle through the passageway, the distal extremity of the elongate member being in communication with the passageway and permitting the distal extremity of the elongate needle to be advanced out of the passageway sideways at an angle with respect to the longitudinal axis, an optical viewing device having a distal extremity with a field of view and means carried by the proximal extremity of the elongate member for mounting the distal extremity of the optical viewing device within the distal extremity of the elongate member and for moving the distal extremity of the optical viewing device relative to the elongate member from a first longitudinal position to permit viewing forward of the elongate member for guiding the distal extremity of the elongate member within the body to a second longitudinal position proximal of the first longitudinal position to permit viewing the distal extremity of the elongate needle as it is advanced from the passageway sideways of the longitudinal axis.

20. A device as in claim 19 wherein the passageway extends to a port at the distal extremity of the elongate member and wherein the first longitudinal position is distal of the port and the second longitudinal position is proximal of the port.

21. A device as in claim 20 wherein the distal extremity of the elongate member has a rounded tip and a transversely extending recess proximal of the rounded tip, the port disposed between the rounded tip and the recess.

22. A device as in claim 19 wherein the elongate needle is a needle electrode, an insulating sleeve coaxially mounted on the needle electrode.

23. A device as in claim 22 together with means mounted on the proximal extremity of the elongate member and connected to the handle means and to the insulating sleeve for causing the insulating sleeve to move relative to the needle electrode.

24. A medical probe device comprising an elongate guide housing having proximal and distal extremities and having a passageway therein extending from the proximal extremity to the distal extremity along a longitudinal axis, a stylet mounted in the guide housing and having proximal and distal extremities, handle means coupled to the proximal extremity of the guide housing, the handle means including means connected to the stylet for causing advancement of the stylet through the passageway, the distal extremity of the guide housing being in communication with the passageway and permitting the distal extremity of the stylet to be advanced out of the passageway sidewise at an angle with respect to the longitudinal axis and an optical viewing device mounted in the guide housing and having a distal extremity positioned in the distal extremity of the guide housing and having a field of view which permits viewing the distal extremity of the stylet as it is advanced from the passageway sidewise of the longitudinal axis.

25. A device as in claim 24 wherein the stylet includes a conductive radio frequency electrode and an insulating sleeve coaxially mounted on the conductive radio frequency electrode and exposing a length of the conductive radio frequency electrode.

26. A device as in claim 24 for use in a human body together with means carried by the proximal extremity of the guide housing for mounting the distal extremity of the optical viewing device within the distal extremity of the guide housing and for moving the distal extremity of the optical viewing device relative to the guide housing from a first longitudinal position to permit viewing forward of the guide housing for guiding the distal extremity of the guide housing within the body to a second longitudinal position proximal of the first longitudinal position to permit viewing the distal extremity of the stylet as it is advanced from the passageway sidewise of the longitudinal axis.

27. A medical probe device for medical treatment of tissue of a prostate in a human body through a urethra defined by a urethral wall comprising an elongate member having proximal and distal extremities and having a passageway therein extending along a longitudinal axis from the proximal extremity to the distal extremity, a stylet mounted in the passageway and having proximal and distal extremities, the stylet including a flexible radio frequency electrode and a layer of insulating material coaxially mounted on the radio frequency electrode, handle means coupled to the proximal extremity of the elongate member for introducing the distal extremity of the elongate member into the body, the handle means including means connected to the stylet for causing advancement of the stylet through the passageway, the distal extremity of the elongate member having means for directing the distal extremity of the stylet out of the passageway sideways at an angle with respect to the longitudinal axis, an optical viewing device having a distal extremity with a field of view and means carried by the proximal extremity of the elongate member for mounting the distal extremity of the optical viewing device within the distal extremity of the elongate member and for moving the distal extremity of the optical viewing device relative to the elongate member from a first longitudinal position to permit viewing forward of the elongate member for guiding the distal extremity of the elongate member within the body to a second longitudinal position proximal of the first longitudinal position to permit viewing the distal extremity of the stylet as it is advanced from the passageway sideways of the longitudinal axis into the tissue of the prostate.

28. A medical probe device as in claim 27 wherein at least a portion of the distal extremity of the elongate member is transparent to permit the optical viewing device to view the distal extremity of the stylet through the distal extremity of the elongate member as it is advanced from the passageway sideways of the longitudinal axis into the tissue of the prostate.

29. A medical probe device for medical treatment of tissue of a prostate through a urethra defined by a urethral wall comprising a guide housing having proximal and distal extremities and having a passageway extending from the proximal extremity to the distal extremity, a stylet for delivering radio frequency energy into the tissue of the prostate mounted in the guide housing, means carried by the distal extremity of the guide housing and in communication with said passageway for directing the stylet sideways of the guide housing, handle means coupled to the proximal extremity of the guide housing for introducing the distal extremity of the guide housing into the urethra into the vicinity of the prostate, said handle means including means secured to the stylet for advancing the stylet from the passageway of the guide housing to cause the stylet to penetrate the urethral wall and to extend into the tissue of the prostate, means for supplying radio frequency energy to the stylet to cause the temperature of the tissue of the prostate adjacent the stylet to be raised to cause destruction of cells in the tissue of the prostate and an optical viewing device positioned in the guide housing having a viewing field that extends forwardly and sidewardly of the guide housing to permit viewing of the stylet as it is deployed sidewise from the distal extremity of the guide housing.

30. A medical probe device for medical treatment of tissue of a prostate through a urethra defined by a urethral wall comprising a guide housing having proximal and distal extremities and having a passageway extending from the proximal extremity to the distal extremity, a stylet mounted in the guide housing, means carried by the distal extremity of the guide housing and in communication with said passageway for directing the stylet sidewise of the guide housing, the stylet including a flexible radio frequency electrode and a layer of insulating material coaxially mounted on the electrode, handle means coupled to the proximal extremity of the guide housing for introducing the distal extremity of the guide housing into the urethra into the vicinity of the prostate, said handle means including means secured to the stylet for advancing the stylet from the passageway of the guide housing to cause the radio frequency electrode and the layer of insulating material to penetrate the urethral wall and to extend into the tissue of the prostate with the layer of insulating material extending through the urethral wall and the radio frequency electrode having a length in the tissue of the prostate for causing the temperature of the tissue of the prostate adjacent the length of the radio frequency electrode to be raised and thus destroy cells in the tissue of the prostate and an optical viewing device positioned in the guide housing having a viewing field that extends forwardly and sidewardly of the guide housing, at least a portion of the distal extremity of the guide housing being transparent to permit the optical viewing device to view the radio frequency electrode and the layer of insulating material through the distal extremity of the guide housing as they are deployed sidewise from the distal extremity of the guide housing.

* * * * *